United States Patent [19]

Shinde et al.

[11] Patent Number: 5,218,296

[45] Date of Patent: Jun. 8, 1993

[54] METHOD AND APPARATUS FOR DETERMINING AT LEAST ONE CHARACTERISTIC OF A SUPERCONDUCTIVE FILM

[75] Inventors: Subhash L. Shinde, Croton-on-Hudson; Thomas K. Worthington, New York, both of N.Y.

[73] Assignee: International Business Machines Corporation, Armonk, N.Y.

[21] Appl. No.: 832,531

[22] Filed: Feb. 7, 1992

[51] Int. Cl.$^5$ ..................... G01R 33/12; G01N 27/72
[52] U.S. Cl. ................................. 324/239; 324/228; 324/262; 505/726
[58] Field of Search .............. 324/236, 239, 228, 262, 324/248, 719, 654, 655, 658, 668, 681, 682; 505/842, 843, 726

[56] References Cited

U.S. PATENT DOCUMENTS

| | | |
|---|---|---|
| 3,192,474 | 6/1965 | Cherry . |
| 3,209,245 | 9/1965 | Hauge . |
| 3,340,467 | 9/1967 | Ha . |
| 3,646,813 | 3/1972 | Kuznietz et al. . |
| 3,747,085 | 7/1973 | Bala et al. . |
| 3,904,956 | 9/1975 | O'Brien et al. . |
| 4,069,714 | 1/1978 | Spewock et al. . |
| 4,507,609 | 3/1985 | Madewell . |
| 4,514,687 | 4/1985 | Van Husen . |
| 4,851,762 | 7/1989 | Kim et al. . |
| 4,864,236 | 9/1989 | Gibson et al. . |
| 4,876,239 | 10/1989 | Cachier . |
| 4,901,016 | 2/1990 | Kusatani et al. . |
| 4,901,017 | 2/1990 | Zinke . |
| 4,904,929 | 2/1990 | Bohandy et al. . |
| 4,906,607 | 3/1990 | Dev Tyagi . |
| 4,931,730 | 6/1990 | Olsen et al. . |
| 4,978,922 | 12/1990 | Mallick, Jr. et al. . |
| 4,996,472 | 2/1991 | Mallick, Jr. . |
| 5,030,912 | 7/1991 | Herko et al. ................. 324/239 |

FOREIGN PATENT DOCUMENTS

| | | |
|---|---|---|
| 64-49980 | 2/1989 | Japan . |
| 64-59169 | 3/1989 | Japan . |
| 1-97876 | 4/1989 | Japan . |
| 1-176939 | 7/1989 | Japan . |
| 1077466 | 3/1982 | U.S.S.R. . |
| 915016 | 12/1986 | U.S.S.R. . |

OTHER PUBLICATIONS

"Magnetization and Meissner Effect in the High $T_c$ Superconductor $Ba_xY_{1-x}CuO_3O_{3-y}$," Electrotechnical Laboratory, by M. Tokumoto et al. Mar. 1987.

*Primary Examiner*—Walter E. Snow
*Attorney, Agent, or Firm*—Perman & Green

[57] ABSTRACT

Disclosed are apparatus and method for measuring a characteristic of a film comprised of a material that is a superconductor below a critical temperature. The apparatus includes a magnetic circuit for inducing an alternating magnetic flux at a localized region of a surface of the film. The circuit includes a magnetic core (42) having a gap (44) made therein and a drive winding (46) coupled thereto. A current source (50) is coupled to the drive winding for passing an alternating current therethrough for inducing an alternating magnetic flux within the gap. Measurement circuitry (54, 56) is responsive to a current induced within the film by an entry of the magnetic flux into the film. A processor (60) is coupled to the measurement circuitry and determines a critical current density of the superconducting film within the localized region. The measurement circuitry includes a sense winding (48) that is coupled to the core and detects a magnitude of an electrical signal induced in the sense winding by the alternating magnetic flux.

19 Claims, 3 Drawing Sheets

METHOD AND APPARATUS FOR DETERMINING AT LEAST ONE CHARACTERISTIC OF A SUPERCONDUCTIVE FILM

FIELD OF THE INVENTION

This invention relates generally to inspection tools and, in particular, to a tool for characterizing one or more properties of a superconducting material.

BACKGROUND OF THE INVENTION

Superconducting materials, or superconductors, have an associated critical temperature ($T_c$) that varies, depending upon the particular superconductor material. When a superconductor is at a temperature that is higher than the associated $T_c$, the superconductor does not conduct electricity in an efficient manner. When the temperature of the superconductor is reduced to below the associated $T_c$, it becomes an efficient conductor of electricity. Superconductors having a relatively low $T_c$ (near 20° Kelvin) have been available for a considerable period of time. More recently, superconductors have been developed which have a relatively high $T_c$ (approximately 90° Kelvin), which is above the temperature of liquid nitrogen (77° Kelvin), thereby permitting such superconductors to be inexpensively maintained below their critical temperatures. Techniques are known for forming, upon suitable substrate material, a thin layer or film of High $T_c$ superconductor material.

However, a technique is required for inspecting the quality of large area superconducting films, particularly films comprised of high transition temperature materials, such as $Y_1Ba_2Cu_3O_y$, before large area devices can be produced with an acceptable yield. In particular, a tool is required to measure the $T_c$, and the critical current density $J_c$, of a superconducting film. The tool measurement resolution should be such that it can be insured that a device fabricated from the film will not be defective because of a defect in the original film.

It is thus one object of the invention to provide apparatus and method for determining at least one characteristic of a superconducting film material.

It is another object of the invention to provide apparatus and method for determining at least one characteristic of a superconducting film material, such as the critical current density and/or the critical temperature, at a localized region of the film.

It is a further object of the invention to provide apparatus and method for determining the presence and location of, and also the spatial extent of, a defect within a superconducting film material.

SUMMARY OF THE INVENTION

Disclosed herein is apparatus and method for testing selected localized regions of a superconductive film for superconducting properties.

The apparatus includes a generally toroidal magnetic circuit made of a magnetically soft material. The magnetic circuit includes a flux concentrating or localizing gap that is adapted to be magnetically coupled to a region of the superconductive film. Drive and sense windings are coupled to the magnetic circuit for magnetically energizing the circuit with an ac drive signal and for sensing the magnetic flux passing through the circuit.

During use, a film of superconductive material is maintained at a desired test temperature. The film is positioned so that a localized region of the film is located proximate to the gap of the magnetic circuit in a position to interrupt flux lines. By example, the superconductive film is inserted within the gap generally perpendicular to the magnetic circuit so that the test region interrupts magnetic flux lines passing across the gap. Alternatively, the superconductive film to be tested may be positioned with the localized region located adjacent to and outside of the gap so that the localized region interrupts magnetic flux lines in a fringe field of the gap. The magnetic circuit is energized with an ac drive signal of appropriate level and frequency that is applied to the drive winding. This causes an alternating magnetic field to appear across the gap of the magnetic circuit.

If the test region of the superconductive film to be tested is in a normal conductive state, at the test temperature, magnetic flux lines of the gap penetrate the film. That is, the magnetic flux lines pass completely through the film. This results in a first level of magnetic flux in the magnetic circuit, relative to the amplitude of the drive signal. The level of magnetic flux in the magnetic circuit is detected by measuring a voltage on the sense winding.

If, instead, the localized region of the film to be tested is superconducting, at the test temperature, magnetic flux of the flux-localization gap does not pass through the film due to the generation of induced supercurrents. However, the magnetic flux will enter the film up to a penetration depth (lambda). In general, this penetration depth is a function of the critical current density of the film and the applied AC field, and is known in the art as the Bean penetration depth. So long as lambda is less than the thickness of the film sample, the AC field does not pass completely through the film. Typically, the film thickness is several thousand Angstroms, whereas the gap spacing, between the magnetic circuit and the film, may be several orders of magnitude greater than the film thickness.

As a result, magnetic flux in the magnetic circuit, relative to a same magnitude of the drive signal, is at a second, lower level that differs from the first level. The voltage obtained from the sense winding thus reflects the difference in levels of magnetic flux in the magnetic circuit and corresponds to the normal and superconducting states of the localized region that is disposed within the gap.

When the apparatus is suitably calibrated, the critical current density ($J_c$) times the thickness (t) at a selected localized region of the superconducting film is measured. To measure $J_c t$, a drive signal of increasing amplitude is applied to the drive winding. As the amplitude of the drive signal increases, the amplitude at which the flux-sensing voltage of the sense winding indicates that the film has switched from a superconducting to a normal state is noted. The switch from the superconducting state to the normal state indicates that the current density induced in the test region of the film by the magnetic field across the gap has exceeded the critical current density ($J_c t$). For a constant film thickness, the measurement is proportional to $J_c$.

The transition temperature $T_c$ may be measured with the apparatus by varying the temperature of the localized region of the film and noting the temperature at which the sensed voltage indicates that the film has switched between the normal and superconducting states.

In accordance with the invention there is disclosed apparatus and method for measuring a characteristic of a film comprised of a material that is superconducting below a critical temperature. The apparatus includes a magnetic circuit for inducing an alternating magnetic flux at a localized region of a surface of the film. The circuit includes a magnetic core having a gap made therein and a drive winding coupled thereto. A current source is coupled to the drive winding for passing an alternating current therethrough for inducing an alternating magnetic flux within the gap. Measurement circuitry is responsive to a current induced within the film by an entry of the magnetic flux into the film. A processor is coupled to the measurement circuitry and determines a critical current density of the superconducting film within the localized region. The measurement circuitry includes a sense winding that is coupled to the core and which detects a magnitude of an electrical signal induced in the sense winding by the alternating magnetic flux.

BRIEF DESCRIPTION OF THE DRAWING

The above set forth and other features of the invention are made more apparent in the ensuing detailed description of the invention when read in conjunction with the attached drawing, wherein.

DETAILED DESCRIPTION OF THE INVENTION

As employed herein, a critical value is considered to be a level of temperature, magnetic field, or current density above which a material ceases to exhibit superconducting properties.

Figure 1:
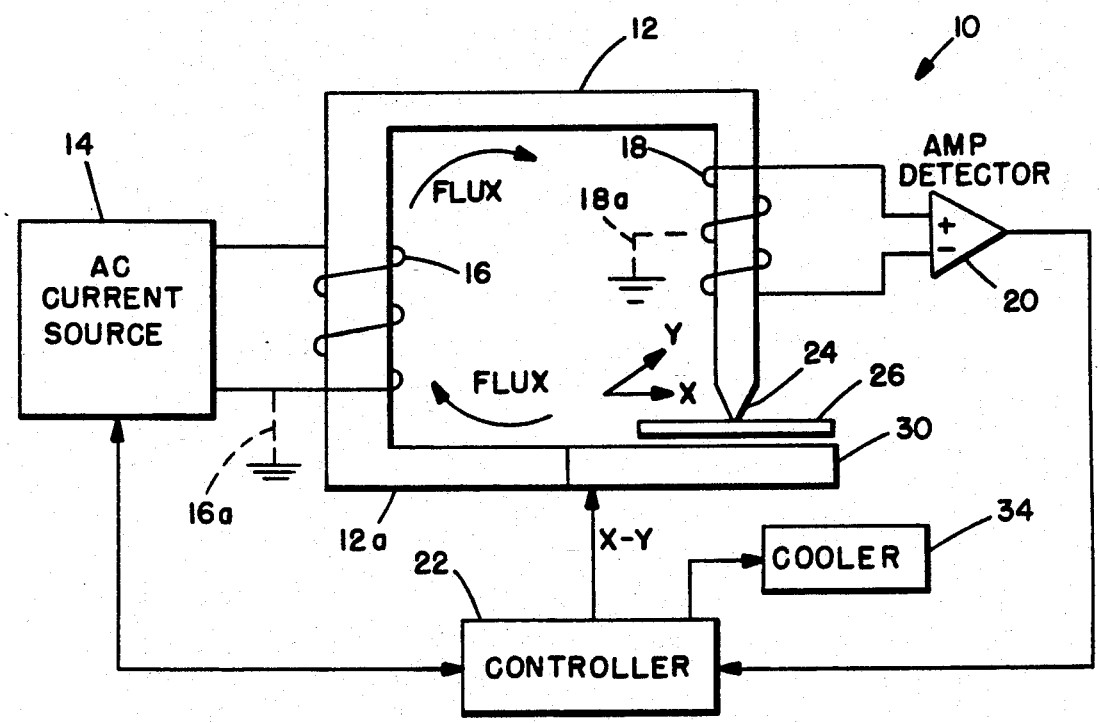
FIG. 1 is a block diagram showing an embodiment of tool constructed in accordance with the invention.
Figure 2:
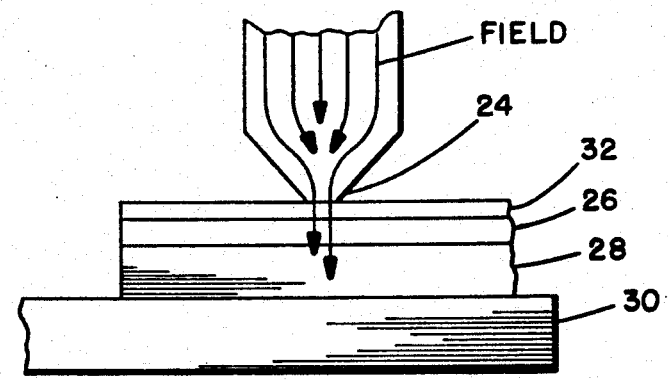
FIG. 2 shows in greater detail the coupling of the tool tip to a film being characterized.

Referring to FIGS. 1 and 2 there is illustrated a test system 10 that is constructed and operated in accordance with the invention. A magnetic containment path includes a generally toroidal core 12 comprised of, by example, a ferrite material. A magnetic flux is induced into the core 12 by an alternating current (ac) current source 14 through a drive winding 16. A sense winding 18 is also coupled to the core 12, the sense winding 18 feeding an amplifier 20. By example, the drive winding 16 and the sense winding 18 are each comprised of approximately 100 turns of wire. The sense winding 18 is optionally center-tapped (18a). The drive winding 16 may be optionally grounded (16a) at one end. The amplifier 20 is, by example, connected in a differential amplifier configuration. The output of the amplifier detector 20 is provided to a controller 22 embodied within, by example, a personal computer or any suitable data processing apparatus. Controller 22 has an output coupled to the ac current source 14 which, in a preferred embodiment of the invention, is a programmable current source that is responsive to commands sent by the controller 22.

In accordance with an embodiment of the invention the core 12 includes a gap bounded on one side by a flux-concentrating pole tip 24, the dimensions of which define the spatial resolution of the system 10. The core 12 contains the magnetic flux and operates to ensure that the reluctance of the system 10 is dominated by the reluctance of the gap. Disposed within the gap is a superconductive layer, or film 26, to be characterized.

As seen more clearly in FIG. 2, the superconductive film 26 is disposed upon a suitable substrate 28.

The substrate 28 is mounted upon an x-y stage 30 which is coupled to the controller 22. The x-y stage 30 receives commands from the controller 22 to translate the substrate 28, and the superconductive film 26, in x and y dimensions.

The pole tip 24 may rest directly upon the surface of the superconductive film 26. Alternately, a thin sheet 32 comprised of, by example, "MYLAR" or "TEFLON" is interposed between the pole tip 24 and the superconductive film 26. It is also within the scope of the invention to provide an air gap between the pole tip 24 and the superconductive film 26. For all of these cases, it is important that the distance between the end of the pole tip 24 and the upper surface of the superconductive film 26 remain approximately constant as the superconductive film 26 is translated beneath the pole tip 24.

The width of the gap is a function of the substrate 28 thickness, which is typically in the range of 30–40 mils, the thickness of the superconductive film, and, if employed, the thickness of the sheet 32 or the desired air gap distance. It is preferred to maintain the pole tip 24 as near to the superconductive film as possible without adversely effecting the surface quality of the superconductive film. For the illustrated embodiment, the pole tip 24 has a terminal dimension of approximately five mils. Generally, and for the case where the pole tip 24 is spaced away from the surface of the superconductive film 26, the pole tip 24 will have a diameter that is approximately equal to the spacing between pole tip 24 and the surface of the superconductive film 26.

A cryogenic cooling device 34 is provided for maintaining the superconductive film at a desired temperature, such as approximately 77° K. The cooling device 34 may also be coupled to the controller 22 such that the temperature can be varied.

In operation, the ac current source 14 provides an alternating current on the order of several tens of milliamps at a frequency of approximately several hundred Hertz to several thousand Hertz. Generally, higher frequencies are desirable because of a corresponding reduction in Signal to Noise ratio. However, at frequencies above a certain threshold, eddy current effects adversely impact the measurement quality. Thus, the preferred frequency is a function of the material being characterized, the magnetic geometry, and other related factors. The alternating current induces a varying magnetic flux within the core 12 that is concentrated by the pole tip 24. Magnetic flux densities in the range of several hundred Gauss to several thousand Gauss are achieved within the gap, when the core 12 is comprised of ferrite material.

When the superconductive film 26 under the pole tip 24 is in a normal (non-superconducting) state, the magnetic field within the gap penetrates the superconductive film 26 and passes completely the film. A return path for the magnetic flux may be provided through the region 12a, although the provision of a return flux path has been found to not be essential to the operation of the invention.

When the superconductive film 26 is in a superconducting state, the alternating magnetic field enters the film to the penetration depth (lambda) but does not pass completely through the film 26. A current is induced within the superconductive film 26 that opposes the magnetic field within the gap. So long as the magnetic field induces a current within the superconductive film 26 that is smaller than $J_c$ times the thickness (t), for the localized region of the superconductive film 26 disposed beneath the pole tip 24, the superconductive film 26 acts as a shorted transformer turn and reduces the flux in the magnetic circuit. This reduces the permeability of the magnetic circuit and thus reduces the voltage induced in sense winding 18 and detected by the amplifier detector 20.

However, when the magnetic field within the gap is sufficient to induce a current within the film 26 that is larger than the critical current, the superconducting film switches to the normal state. The magnetic field lines then pass through the superconductive film 26, returning the reluctance to the normal state value. As a result, the voltage detected by the amplifier detector 20 increases to the normal state voltage value.

The controller 22 operates to detect such transitions of the output of the amplifier detector 20 so as to characterize the critical current density of the localized region of the superconductive film 26 beneath the pole tip 24. By translating the superconductive film 26 relative to the pole tip 24, the critical current density of the superconductive film 26 is determined at a plurality of localized regions across the surface of the film. Using the dimensions described above a spatial resolution of approximately 0.1 millimeters (approximately 5 mils) is achieved.

Figure 4A:
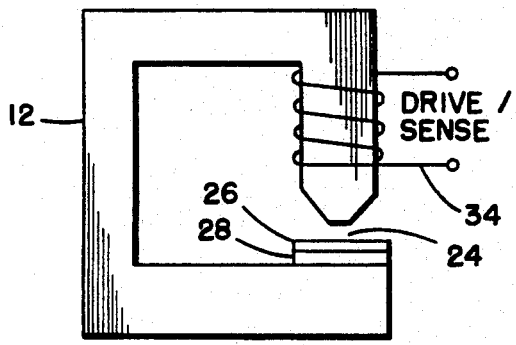
FIGS. 4a and 4b each illustrate an alternate magnetic geometry for the superconducting film measurement system.

It is also within the scope of the invention to employ but a single drive/sense coil 34 that measures the inductance of the coil as a function of current. This magnetic geometry is shown in FIG. 4a.

Figure 4B:
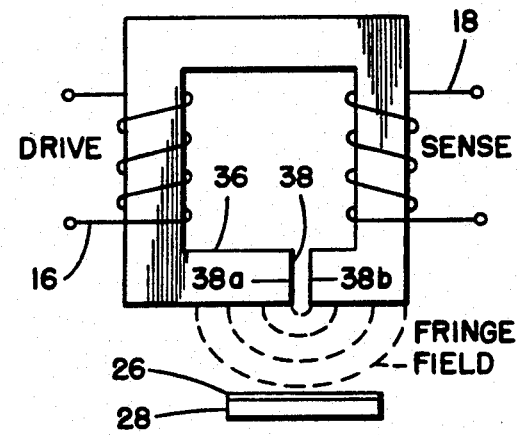

FIG. 4b shows a further embodiment of a ferrite core 36 having a gap 38. The film 26 is thus exposed to a fringe field of the gap 38. The resolution is determined by the flux leakage from the pole pieces 38a and 38b.

Figure 3:
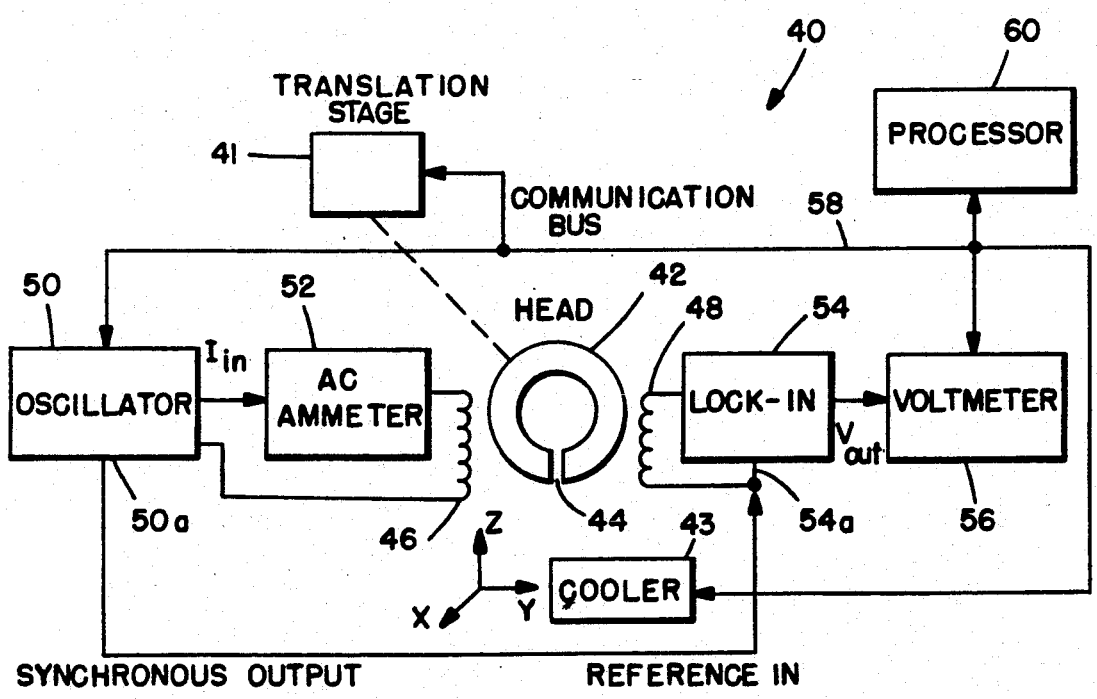
FIG. 3 is a block diagram of a critical current measurement system that is constructed and operated in accordance with the invention.

FIG. 3 is a block diagram of a critical current measurement system 40 that is constructed and operated in accordance with the invention. System 40 includes a ferrite magnetic head 42, similar to the embodiment of FIG. 4b, having a toroidal shape and a gap 44. The width of the gap 44 is approximately five micrometers, and the outer diameter of the magnetic head 42 is approximately 0.2 inches, or five millimeters. During use the gap 44 is positioned closely adjacent to a superconductive film 26 under test (not shown). The magnetic head 42 is coupled to a translation stage 41 for positioning the magnetic head 42 along x-y-z axes. Alternately, the head 42 may be fixed and the superconductive film 26 translated relative to the head. Coupled to magnetic head 42 is a drive winding 46 and a sense winding 48. Drive winding 46 is driven by an oscillator 50 through an ac ammeter 52. During use, a nominal frequency of the oscillator 50 is 1,000 Hz. Oscillator 50 provides current in the range of one to 50 milliamps r.m.s. to the head 40. The sense winding 48 is coupled to a lock-in amplifier 54, which receives a reference input 54a from a synchronous output 50a of the oscillator 50. For the given range of currents, the output of lock-in amplifier 54 is in the range of approximately zero volts to approximately two millivolts. A voltmeter 56 is coupled to an output of the lock-in amplifier 54 for measuring this output voltage.

Bidirectionally coupled by a communication bus 58 to the oscillator 50 and the voltmeter 56 is a processor 60. Processor 60 controls the frequency and output current of the oscillator 50, and also communicates with voltmeter 56 to receive voltage readings ($V_{OUT}$) therefrom. Processor 60 converts these readings to permeability or other suitable indications of the magnetic properties of the superconductive thin film under test. The translation stage 41, and also a cryogenic cooler 43, may also be coupled to the processor 60 via the communication bus 58.

By example only, the communication bus 58 conforms to the well-known IEEE-488 standard, and the processor 60 is embodied in a personal computer having an IEEE-488 interface card.

Figure 5:
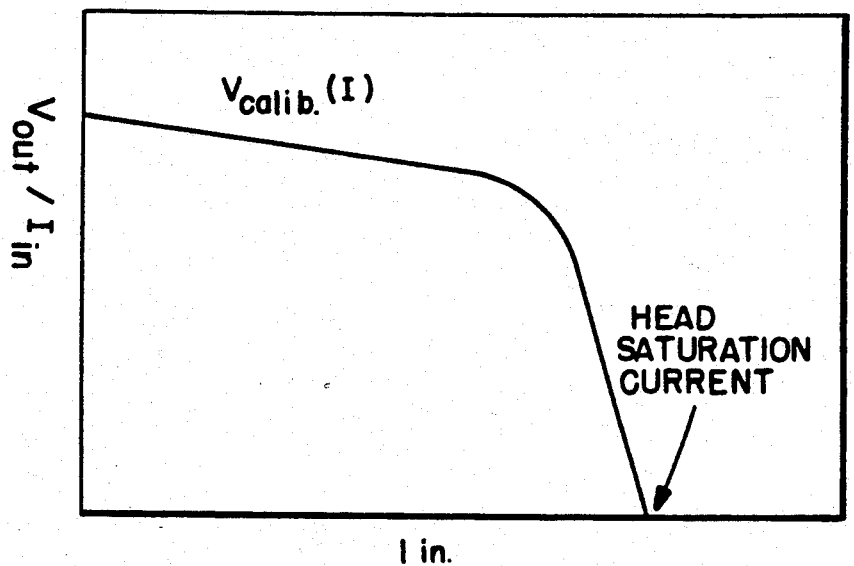
FIG. 5 illustrates an exemplary calibration curve for the measurement system of FIG. 3.

FIG. 5 illustrates an exemplary calibration curve for the measurement system of FIG. 3. The calibration curve is obtained without a superconductive film sample and plots $V_{OUT}/I_{IN}$ as a function of $I_{IN}$, up to the saturation current of the magnetic head 42.

Figure 6:
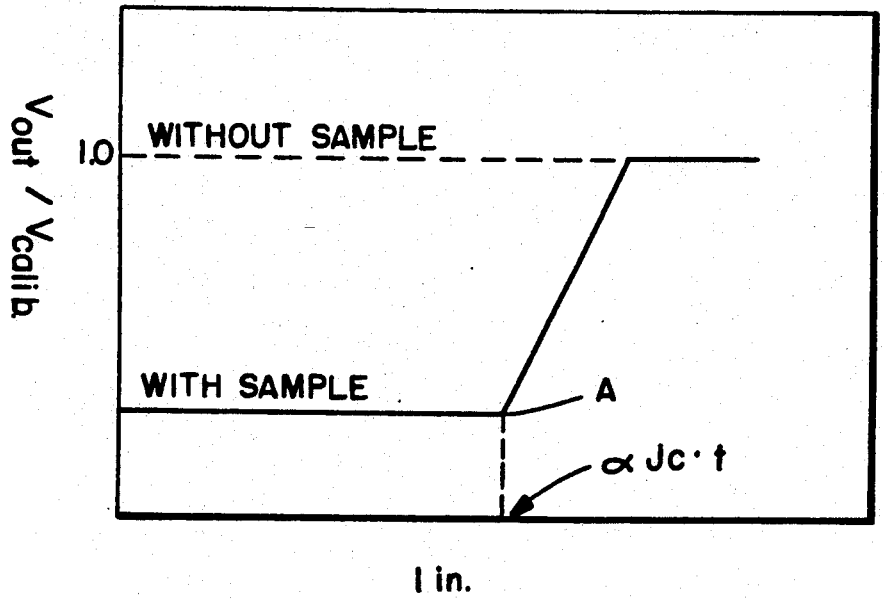
FIG. 6 illustrates a $J_c$ measurement for a superconducting thin film obtained with the measurement system of FIG. 3.

FIG. 6 illustrates a $J_c t$ measurement for a superconductive thin film obtained with the measurement system of FIG. 3. The value of $I_{IN}$, for which the non-linearity (A) appears, is proportional to both $J_c$ and the thickness (t) of the superconductive thin film. Thus, if $J_c$ is known a priori, then the thickness of the thin film is determinable. Conversely, if the thickness is known, then $J_c$ is determinable. It is also within the scope of the invention to determine a value of input current to maintain a localized region of a superconductive film below its $J_c$, and to vary the temperature of the film with cryogenic cooler 43 so as to determine the $T_c$ of the film. The $T_c$ is determined when the film switches from the superconducting state to the normal state, as evidenced by an increase in the permeability of the film.

Figure 7:
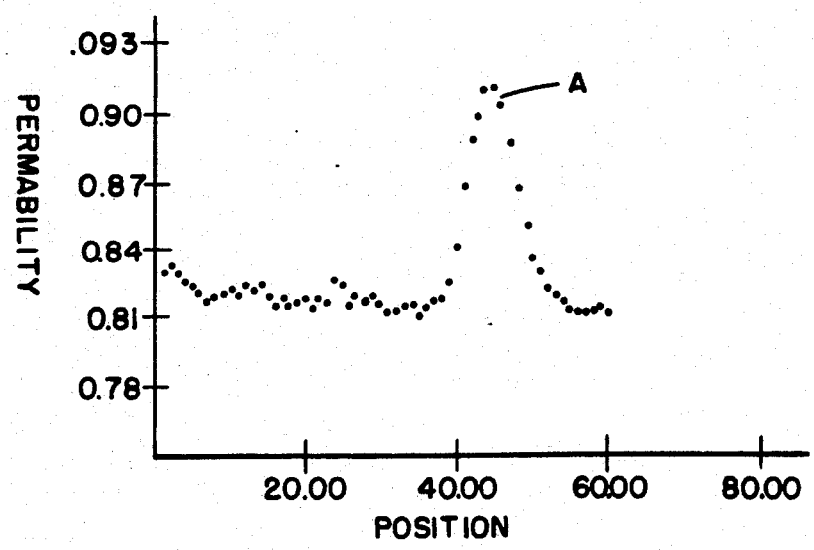
FIG. 7 is a graph of permeability vs. position upon a surface of a superconducting thin film, and shows the detection of a film defect.

FIG. 7 is a graph of permeability vs. position upon a surface of a superconducting thin film, and shows the detection of a film non-uniformity or defect, specifically a scratch, at a determined location upon the film. In accordance with an aspect of the invention, an $I_{IN}$ value is selected that imposes a $J_{cI}$ upon the film sample, and the magnetic head 42 is scanned over the surface of the superconducting film. Defective regions, characterized as having a $J_c$ less than $J_{cI}$, exhibit a change in $V_{OUT}/V_{calib}(I_{IN})$. As such, the processor 60 is enabled to record the positions of defects with a spatial resolution determined by the dimensions of the magnetic head 42 and the flux leakage. The spatial resolution for the graph of FIG. 7 is approximately 150 micrometers.

As can be seen in FIG. 7, the measured permeability of the superconducting film is substantially constant from position 00.00 to approximately 40.00. At this point the permeability suddenly rises (point A), indicating a reduction in the superconducting properties of the superconducting thin film. As the head 42 passes over the non-uniformity, the permeability drops back to the previously obtained superconducting state value (approximately 0.83). As such, the presence, location, and spatial extent of the non-uniformity are determinable by the processor 60 from the magnitude of $V_{OUT}$. Permeability is proportional to $V_{OUT}$ divided by $V_{CALIB}$.

While the invention has been particularly shown and described with respect to preferred embodiments thereof, it will be understood by those skilled in the art that changes in form and details may be made therein without departing from the scope and spirit of the invention.

Having thus described our invention, what we claim as new, and desire to secure by Letters Patent is:

1. Apparatus for measuring a characteristic of a film comprised of a material that is a superconductor below a critical temperature, comprising:
    means for maintaining the film at a temperature such that the film is in a superconducting state;
    means for inducing an alternating magnetic flux at a localized region of a surface of the film, said inducing means being responsive to a control input signal for varying a magnitude of the magnetic flux; and
    means, responsive to a current induced within the film by an entry of the magnetic flux into the film, for determining a critical current density of the film within the localized region.

2. Apparatus as set forth in claim 1 wherein said inducing means includes:
    core means having a gap, the gap having a width sufficient to accommodate the film therein and being bounded at one side by a pole tip adapted for concentrating the magnetic flux within the gap, said core means including a drive winding coupled thereto; and
    current source means coupled to said drive winding for passing an alternating current of variable magnitude therethrough for inducing an alternating magnetic flux within the gap.

3. Apparatus as set forth in claim 2 wherein said core means further includes a sense winding coupled thereto, and wherein said determining means includes means for detecting a magnitude of an electrical signal induced in said sense winding by said alternating magnetic flux.

4. Apparatus as set forth in claim 3 wherein said drive winding and said sense winding are two separate windings.

5. Apparatus as set forth in claim 3 wherein said drive winding and said sense winding are a single winding.

6. Apparatus as set forth in claim and further including means for translating the film relative to the determining means so that the critical current density of the film is determinable within a plurality of localized regions.

7. Apparatus as set forth in claim 1 wherein said inducing means includes:
    core means having a gap, said core means including a drive winding coupled thereto; and
    current source means coupled to said drive winding for passing an alternating current of variable magnitude therethrough for inducing an alternating magnetic flux within and around the gap.

8. Apparatus for measuring a characteristic of a film comprised of a material that is a superconductor below a critical temperature, comprising:
    means for maintaining the film at a temperature such that the film is in a superconducting state;
    means for inducing an alternating magnetic field at a localized region of a surface of the film, said inducing means including,
    a magnetic path confining means having a gap made therein, said magnetic path confining means having a drive winding coupled thereto; and
    current source means coupled to said drive winding for passing an alternating current therethrough for inducing an alternating magnetic field within the gap, said current source means being responsive to a control input signal for varying an amplitude of the alternating current so as to vary a magnitude of the alternating magnetic field;
    means, responsive to a current induced within the film by an entry of the magnetic field into the film, for determining a critical current density of the film within the localized region, said determining means including,
    a sense winding coupled to said magnetic path confining means; and
    means for detecting a magnitude of an electrical signal induced in said sense winding by said alternating magnetic field; said apparatus further comprising;
    means for translating the film relative to the determining means so that the critical current density of the film is determinable within a plurality of localized regions of the film.

9. Apparatus as set forth in claim 8 wherein said drive winding and said sense winding are two separate windings.

10. Apparatus as set forth in claim 8 wherein said drive winding and said sense winding are a single winding.

11. A method of detecting a presence of a non-uniformity within a superconducting film, comprising the steps of:
    maintaining the film at a temperature such that the film is in a superconducting state;
    inducing an alternating magnetic field at a localized region of a surface of the film;
    responsive to a current induced within the film by an entry of the magnetic field into the film, determining a critical current density of the film within the localized region;
    determining, from the critical current density, a superconducting state permeability of the film;
    measuring the permeability of a magnetic circuit that includes the film, at a plurality of localized regions, by inducing the alternating magnetic field at a plurality of localized regions of the film, the alternating magnetic field being provided so as to induce a current density within the film that is less than the determined critical current density; and
    observing the measured permeability to detect a localized region wherein the measured critical current multiplied by the thickness of the film deviates from the determined superconducting state critical current, the deviation being due to a non-uniformity of the superconducting film within the localized region.

12. A method as set forth in claim 11 wherein the step of inducing an alternating magnetic flux includes a step of:
    disposing a gapped magnetic core means in proximity to the superconducting film; and
    energizing the gapped magnetic core means with an alternating current.

13. A method as set forth in claim 12 wherein the step of measuring includes a step of translating the superconducting film relative to the gapped magnetic core means.

14. A method for measuring a critical current density ($J_c$) at a selected region of a superconductive film, comprising the steps of:
  maintaining the film at a temperature so that the film is in a superconducting state;
  disposing a selected region of the film in proximity to an alternating magnetic field;
  detecting a magnitude of a current induced in the selected region of the film by the magnetic field;
  increasing the strength of the magnetic field so as to increase the magnitude of the induced current; and
  monitoring an amount of magnetic flux that is coupled into the selected region of the film to determine a magnitude of the current density at which the film switches from the superconducting state to a normal state, the determined magnitude of the current density being equal to $J_c$.

15. A method for measuring a critical temperature ($T_c$) at a selected region of a superconductive film, comprising the steps of:
  maintaining the film at a first temperature so that the film is in a superconducting state;
  disposing the selected region of the film in proximity to an alternating magnetic field;
  detecting a magnitude of a current induced in the selected region of the film by the alternating magnetic field;
  monitoring an amount of magnetic flux that is coupled into the selected region of the film to determine a magnitude of the current density at which the film switches from the superconducting state to a normal state, the determined magnitude of the current density being equal to $J_c$;
  providing the alternating magnetic field so as to induce into the selected region of the film a current that is less than $J_c$; and
  varying the temperature of the film from the first temperature to determine a temperature at which the selected region of the film switches from the superconducting state to a normal state, the determined temperature being equal to $T_c$.

16. Apparatus for detecting a presence of a non-uniformity within a superconducting film, comprising:
  means for maintaining the film at a temperature so that the film is in a superconducting state;
  means for inducing an alternating magnetic field at a localized region of a surface of the film;
  measurement means, responsive to a current induced within the film by an entry of the magnetic field into the film, for determining a critical current density of the film within the localized region and for determining, from the critical current density, a superconducting state permeability of the film;
  said measurement means including means for measuring the permeability of a magnetic circuit that includes the film, at a plurality of localized regions of the film, by inducing the alternating magnetic field at a plurality of localized regions of the film, the alternating magnetic field being provided so as to induce a current density within the film that is less than the determined critical current density; and
  means, responsive to the measured permeability, for identifying a localized region wherein the measured critical current, when multiplied by the thickness of the film, deviates from the determined superconducting state critical current, the deviation being due to a non-uniformity of the superconducting film within the localized region.

17. Apparatus for measuring a critical temperature ($T_c$) at a selected region of a superconductive film, comprising:
  means for maintaining the film at a first temperature so that the film is in a superconducting state;
  means for generating an alternating magnetic field at a selected region of a surface of the film;
  means for detecting a magnitude of a current induced in the selected region of the film by the magnetic field;
  means for monitoring an amount of magnetic flux that is coupled into the selected region of the film, said monitoring means being responsive to an output of said detecting means to determine a magnitude of a current density at which the film switches from a superconducting state to a normal state, the determined magnitude of the current density being equal to $J_c$; and
  means for controlling said generating means to generate the alternating magnetic field so as to induce a current into the selected region of the film that is less than $J_c$, said controlling means further being operable for controlling said establishing means to vary the temperature of the film from the first temperature to determine a temperature at which the selected region of the film switches from the superconducting state to a normal state, the determined temperature being equal to $T_c$.

18. Apparatus as set forth in claim 1 wherein the alternating magnetic flux has a frequency (f), wherein said inducing means includes a magnetic core means having a sense winding coupled thereto, and wherein said determining means includes means for detecting a magnitude of an electrical signal, at the frequency (f), that is generated in said sense winding by the alternating magnetic flux.

19. Apparatus as set forth in claim 8 wherein the alternating magnetic field has a frequency (f), and wherein said detecting means includes means for detecting a magnitude of an electrical signal, at the frequency (f), that is generated in said sense winding by the alternating magnetic field.

* * * * *

UNITED STATES PATENT AND TRADEMARK OFFICE
CERTIFICATE OF CORRECTION

PATENT NO. : 5,218,296

DATED : June 8, 1993

INVENTOR(S) : Shinde et al.

It is certified that error appears in the above-identified patent and that said Letters Patent is hereby corrected as shown below:

Col. 7, line 45, Claim 6, after "claim" insert --1--.

Signed and Sealed this

Eleventh Day of January, 1994

Attest:

BRUCE LEHMAN

Attesting Officer

Commissioner of Patents and Trademarks